(12) United States Patent
Rehkemper (10) Patent No.: US 7,055,531 B2
(45) Date of Patent: Jun. 6, 2006

(54) ELECTRONIC ORAL CLEANING DEVICE (75) Inventor: Steven Rehkemper, Chicago, IL (US)

(73) Assignee: Rehco, LLC, Chicago, IL (US)

( * ) Notice: Subject to any disclaimer, the term of this patent is extended or adjusted under 35 U.S.C. 154(b) by 0 days.

(21) Appl. No.: 10/886,235

(22) Filed: Jul. 7, 2004

(65) Prior Publication Data
US 2006/0005854 A1 Jan. 12, 2006

(51) Int. Cl.
A61C 15/00 (2006.01)

(52) U.S. Cl. ............. 132/322; 132/309; 15/167.1

(58) Field of Classification Search ........ 132/322–324; 15/167.1, 22.1, 25, 26; 433/118, 143
See application file for complete search history.

(56) References Cited

U.S. PATENT DOCUMENTS

| 2,196,667 | A |   | 4/1940  | Moseley           |         |
|-----------|---|---|---------|-------------------|---------|
| 3,400,417 | A |   | 9/1968  | Moret             |         |
| 3,759,274 | A |   | 9/1973  | Warner            |         |
| 3,847,168 | A |   | 11/1974 | Schlegel          |         |
| 3,927,686 | A | * | 12/1975 | Zambito           | 132/323 |
| 4,203,431 | A |   | 5/1980  | Abura et al.      |         |
| 4,235,253 | A | * | 11/1980 | Moore             | 132/322 |
| 4,245,658 | A |   | 1/1981  | Lecouturier       |         |
| 4,307,740 | A |   | 12/1981 | Florindez et al.  |         |
| 4,458,702 | A |   | 7/1984  | Grollimund        |         |
| 4,605,025 | A |   | 8/1986  | McSpadden         |         |
| 4,880,382 | A | * | 11/1989 | Moret et al.      | 433/118 |
| 5,033,150 | A | * | 7/1991  | Gross et al.      | 15/22.1 |
| D323,721  | S |   | 2/1992  | Bushberger        |         |
| 5,120,225 | A |   | 6/1992  | Amit              |         |
| 5,170,809 | A | * | 12/1992 | Imai et al.       | 132/322 |
| 5,226,206 | A |   | 7/1993  | Davidovitz et al. |         |
| 5,232,002 | A |   | 8/1993  | McClallen         |         |
| 5,253,382 | A |   | 10/1993 | Beny              |         |
| 5,261,430 | A | * | 11/1993 | Mochel            | 132/322 |
| 5,274,870 | A |   | 1/1994  | Stollman          |         |
| 5,279,314 | A | * | 1/1994  | Poulos et al.     | 132/322 |
| 5,311,633 | A |   | 5/1994  | Herzog et al.     |         |
| 5,323,796 | A |   | 6/1994  | Urso              |         |
| 5,341,534 | A |   | 8/1994  | Serbinski et al.  |         |
| 5,343,883 | A | * | 9/1994  | Murayama          | 132/322 |
| 5,353,460 | A |   | 10/1994 | Bauman            |         |
| 5,359,747 | A |   | 11/1994 | Amakasu           |         |
| 5,378,153 | A |   | 1/1995  | Giuliani et al.   |         |
| 5,396,678 | A |   | 3/1995  | Bredall et al.    |         |
| 5,404,608 | A |   | 4/1995  | Hommann           |         |
| 5,411,041 | A | * | 5/1995  | Ritter            | 132/322 |
| 5,416,942 | A |   | 5/1995  | Baldacci et al.   |         |

(Continued)

FOREIGN PATENT DOCUMENTS

DE          8708369.8          10/1987

(Continued)

OTHER PUBLICATIONS

US 5,270,314, 12/1993, Populos et al. (withdrawn)

Primary Examiner—Kevin Shaver
Assistant Examiner—Stephanie L. Willatt (57) ABSTRACT In one embodiment of the present invention, an electric oral cleaning device is provided and includes a handle and a power supply contained therein. The device has a motor that drives a motor linkage, which includes a push rod that has one end that engages and moves a dental cleaning head about a center pin to cause an oscillation motion of the head. The entire head assembly is also interchangeable such that a flossing tool and various brushing tools may be utilized by the same device.

9 Claims, 9 Drawing Sheets

U.S. PATENT DOCUMENTS

| | | |
|---|---|---|
| 5,435,034 A | 7/1995 | Bigler et al. |
| 5,461,744 A | 10/1995 | Merbach |
| 5,494,252 A | 2/1996 | Amet et al. |
| 5,504,959 A | 4/1996 | Yukawa et al. |
| 5,524,312 A | 6/1996 | Tan et al. |
| 5,579,786 A | 12/1996 | Wolk et al. |
| 5,590,434 A | 1/1997 | Imai |
| 5,617,601 A | 4/1997 | McDougall |
| 5,617,603 A | 4/1997 | Mei |
| 5,625,916 A | 5/1997 | McDougall |
| 5,636,988 A | 6/1997 | Murayama |
| 5,647,385 A | 7/1997 | Zebuhr |
| RE35,712 E | 1/1998 | Murayama |
| 5,726,932 A | 3/1998 | Lee et al. |
| 5,732,432 A | 3/1998 | Hui |
| 5,732,433 A | 3/1998 | Gocking et al. |
| 5,749,380 A | 5/1998 | Zebuhr |
| 5,784,743 A | 7/1998 | Shek |
| 5,816,271 A | 10/1998 | Urso |
| 5,822,821 A | 10/1998 | Sham |
| 5,836,030 A | 11/1998 | Hazeu et al. |
| 5,839,148 A | 11/1998 | Volpenhein |
| 5,842,244 A | 12/1998 | Hilfinger et al. |
| 5,850,655 A | 12/1998 | Gocking et al. |
| 5,853,290 A | 12/1998 | Winston |
| 5,855,216 A | 1/1999 | Robinson |
| 5,867,856 A | 2/1999 | Herzog |
| 5,901,397 A | 5/1999 | Hafele et al. |
| 5,921,254 A * | 7/1999 | Carlucci et al. ............ 132/322 |
| 5,944,033 A * | 8/1999 | Robinson ................... 132/322 |
| 5,996,157 A | 12/1999 | Smith et al. |
| RE36,699 E * | 5/2000 | Murayama ................. 433/118 |
| 6,447,293 B1 * | 9/2002 | Sokol et al. ................ 433/118 |
| 6,721,986 B1 | 4/2004 | Zhuan |
| D493,577 S | 7/2004 | Winkler |
| 2001/0004781 A1 | 6/2001 | Blaustein et al. |
| 2001/0022277 A1 | 9/2001 | Blaustein et al. |
| 2002/0017474 A1 | 2/2002 | Blaustein et al. |
| 2002/0020645 A1 | 2/2002 | Blaustein et al. |
| 2002/0029988 A1 | 3/2002 | Blaustein et al. |
| 2002/0032941 A1 | 3/2002 | Blaustein et al. |
| 2002/0038772 A1 | 4/2002 | Blaustein et al. |
| 2002/0078514 A1 | 6/2002 | Blaustein et al. |
| 2002/0106607 A1 | 8/2002 | Horowitz |
| 2002/0152564 A1 | 10/2002 | Blaustein et al. |
| 2002/0162180 A1 | 11/2002 | Blaustein et al. |
| 2002/0170570 A1 | 11/2002 | Bergman |
| 2002/0178519 A1 | 12/2002 | Zarlengo |
| 2002/0185149 A1 | 12/2002 | Ali |
| 2003/0031979 A1 | 2/2003 | Shortt et al. |
| 2003/0064348 A1 | 4/2003 | Sokol et al. |
| 2003/0098037 A1 | 5/2003 | Dougan et al. |
| 2003/0101526 A1 | 6/2003 | Hilscher et al. |
| 2003/0140435 A1 | 7/2003 | Eliav et al. |
| 2003/0140437 A1 | 7/2003 | Eliav et al. |
| 2003/0162146 A1 | 8/2003 | Shortt et al. |
| 2003/0182746 A1 | 10/2003 | Fattori et al. |
| 2003/0196677 A1 | 10/2003 | Wiseman |
| 2003/0226575 A1 | 12/2003 | Lee |
| 2004/0035439 A1 | 2/2004 | Lai et al. |
| 2004/0035440 A1 | 2/2004 | Cheng |
| 2004/0040571 A1 | 3/2004 | Williams |
| 2004/0074026 A1 | 4/2004 | Blaustein et al. |
| 2004/0079384 A1 | 4/2004 | Lai et al. |
| 2004/0088807 A1 | 5/2004 | Blaustein et al. |
| 2004/0134512 A1 | 7/2004 | Ding et al. |
| 2005/0076933 A1 * | 4/2005 | Getgey et al. ............... 132/322 |

FOREIGN PATENT DOCUMENTS

| | | |
|---|---|---|
| EP | 0537 465 | 4/1993 |
| EP | 0596 606 | 8/1997 |
| EP | 0990 424 | 5/2000 |
| EP | 1053 721 | 11/2000 |
| GB | 2 228 861 | 9/1990 |
| GB | 2 290 224 | 12/1995 |
| WO | WO 93/20777 | 10/1993 |
| WO | WO 94/09676 | 5/1994 |
| WO | WO 95/31123 | 11/1995 |
| WO | WO 98/26730 | 6/1998 |
| WO | WO 98/46103 | 11/1998 |
| WO | WO 99/12492 | 3/1999 |
| WO | WO 99/65359 | 12/1999 |

* cited by examiner

ELECTRONIC ORAL CLEANING DEVICE

FIELD OF THE INVENTION

The present invention relates to oral cleaning devices used to clean a user's mouth.

CROSS REFERENCE TO RELATED APPLICATIONS

This application claims benefit to U.S. Provisional Application, Serial number to be assigned, entitled "Electric Oral Cleaning Device," and filed on Jun. 25, 2004.

BACKGROUND OF THE INVENTION

Oral cleaning devices, both electric and non-electric, are known in the industry and in the prior art. Numerous patents have issued throughout the years to cover various improvements and novel features in the oral cleaning industry. For example, U.S. Pat. No. 5,170,809 requires a dental floss to be reciprocated along an axis substantially parallel to the axis of a handle (if the dental floss apparatus is positioned upright, the floss would be moving in an up and down motion). Alternatively, the motor mechanism moves a shaft in the handle only along the handle's longitudinal axis, which would impart the same movement in the dental floss attached to the shaft (again, the motion would be an up and down motion if the apparatus is standing in an upright position). U.S. Pat. No. Re. 35,712 discloses a sonic dental device that includes a flossing head that stores extra dental floss such that a user may exchange used dental floss with new floss. U.S. Pat. No. 5,323,796 is directed to an automated dental flosser that includes a twine of floss held in the body of the device for which a user may dispense unused floss.

A common way to move oral cleaning heads (including flossing heads and brush heads) is done by vibrating the end of the neck of the device, such that the head vibrates or moves with the movement of the neck. The present invention provides for a different movement that may be beneficial to the user. The present invention also provides, in one embodiment, an electric oral cleaning device that includes interchangeable heads and provides for an oscillating head that may include a flossing tool or various brush head designs.

SUMMARY OF THE INVENTION

In accordance with an embodiment of the present invention, an electric oral cleaning device is provided that includes various interchangeable heads. In one aspect, the interchangeable head is a flossing head with a removable flossing tool, such that when used the flossing tool may be removed, discarded, and replaced with a new flossing tool. The electric oral cleaning device has a motor that drives a cam. Engaged to the cam is a carrier, which transposes rotational motion of the cam to a side-to-side motion. The carrier engages a rod that includes a fulcrum secured at a point along the length thereof. The other end of the rod is in communication with one of the interchangeable heads. The head includes a section that is moveably connected thereto. As the cam rotates, the second end of the rod moves in a side-to-side direction that pushes against walls secured on the moveable section of the head. As the rod contacts the walls, the moveable section oscillates counterclockwise and clockwise about a pin.

In other aspects of the present invention, the interchangeable heads may include sections utilized to clean other parts of the user's mouth, such as but not limited to the teeth and tongue.

Numerous other advantages and features of the invention will become readily apparent from the following detailed description of the invention and the embodiments thereof and from the accompanying drawings.

BRIEF DESCRIPTION OF THE DRAWINGS

A fuller understanding of the foregoing may be had by reference to the accompanying drawings, wherein:

FIG. 8b is a back perspective view of the flossing head assembly from FIG. 8a;

DETAILED DESCRIPTION OF THE EMBODIMENTS

While the invention is susceptible to embodiments in many different forms, there are shown in the drawings and will be described herein, in detail, the preferred embodiments of the present invention. It should be understood, however, that the present disclosure is to be considered an exemplification of the principles of the invention and is not intended to limit the spirit or scope of the invention to the embodiments illustrated.

Referring now to FIGS. 1 through 4 and in accordance to a first embodiment, an electric oral cleaning device is illustrated and generally referenced to as 100. The first device 100 includes a handle section 102 that a user grasps during use of the device 100. The handle section 102 houses a power supply 104 (such as a battery), which is in electrical communication with an activation button 106 and a motor 108. The motor 108 drives a linkage mechanism 110 that converts the rotational movement of the motor 108 to a back and forth ("oscillating") motion of a cleaning tool 112 (discussed in detail below).

Figure 1:
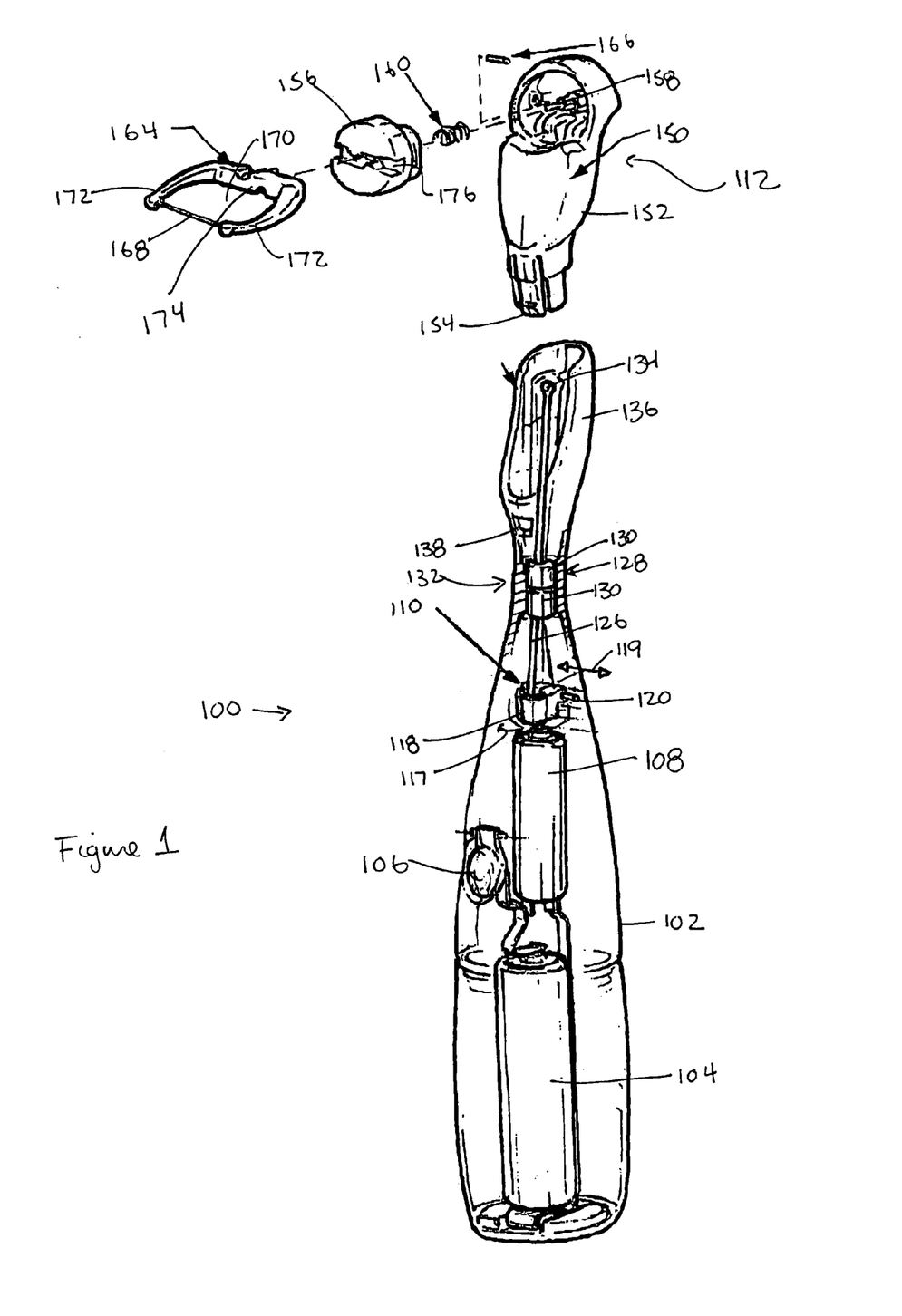
FIG. 1 is a partially exploded perspective view that also illustrates the internal components of a first electric oral cleaning device.
Figure 3:
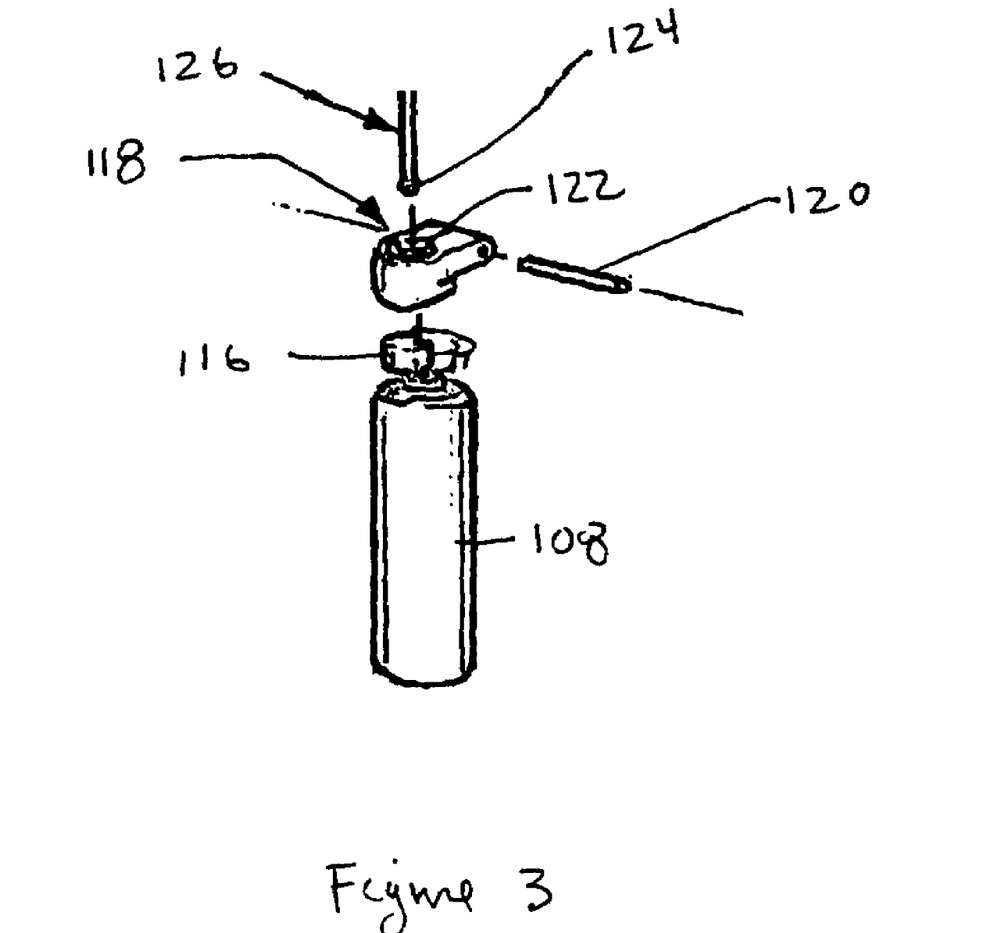
FIG. 3 is a perspective view of the motor mechanism and rotary to linear motion linkage utilized in the device of FIG. 1.

The linkage mechanism 110 includes a cam 116 secured to the drive shaft 114 of the motor 108. A carrier 118 is slidably attached on a pin 120 to the handle 102. The carrier includes apertures on the bottom portion (not shown) and on the top portion (aperture 122). The aperture on the bottom portion is sized such that the carrier 118 sits directly on the cam 116. The aperture 122 on the top portion of the carrier 118 is sized to receive a first end 124 of a rod 126. The linkage mechanism 110 further includes a fulcrum 128 secured along the length of the rod 126. Preferably, the fulcrum is a pair of bushings 130. The rod 126 extends through a neck 132 of the device 100 and has a second end 134 that extends into a head support 136. As the cam 116 rotates (arrows 117), the carrier 118 slides side-to-side (arrows 119); as such the rotational motion is converted to a side-to-side motion. The side-to-side motion on the first end 124 of the rod 126 is moved along the length of the rod 126 through the fulcrum 128 to the second end 134. Thus, when the motor 108 is activated, the second end 134 of the rod 126 will move side-to-side, preferably at very high speeds.

Figure 2:
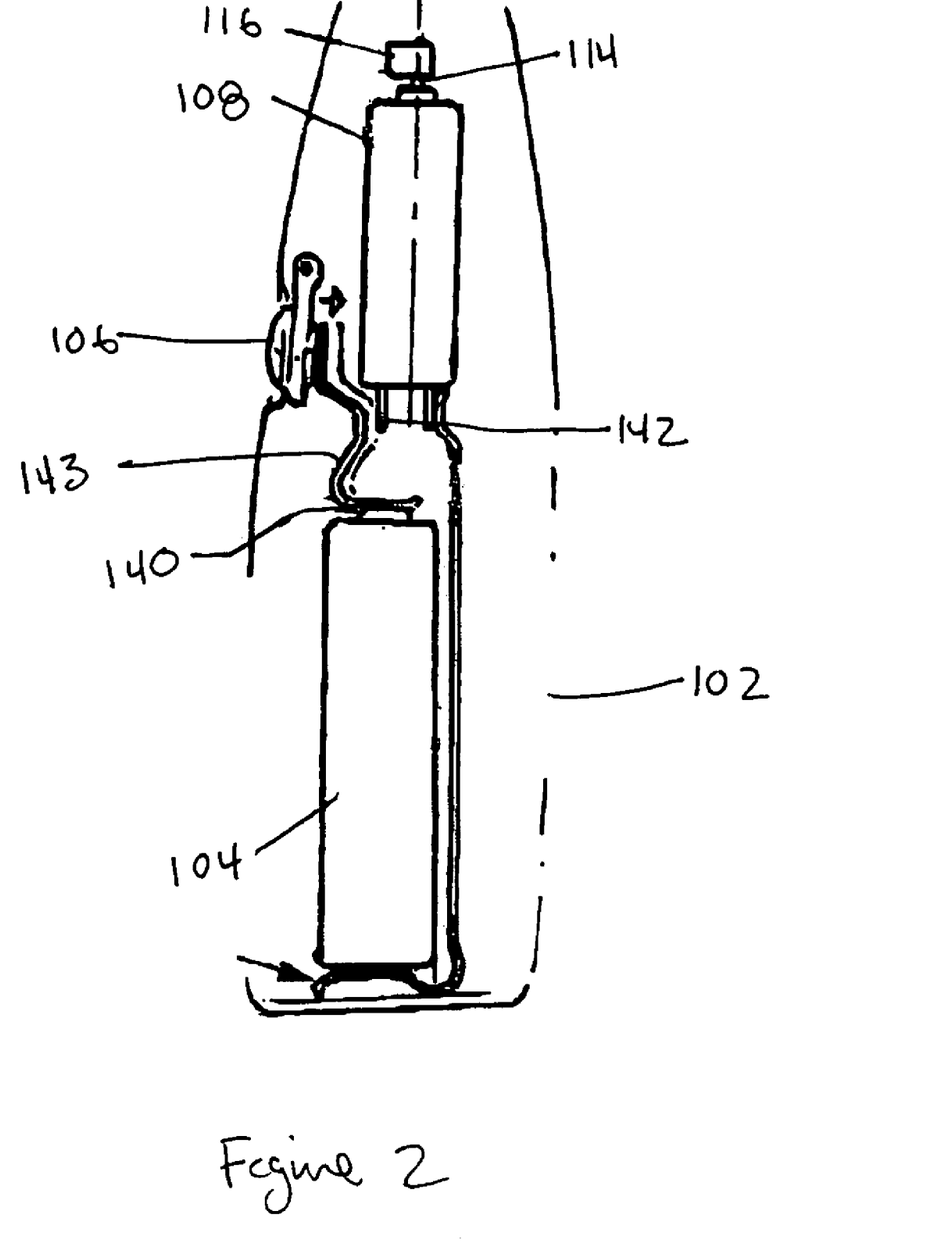
FIG. 2 is a side view of the activation button of the device illustrated in FIG. 1.

As illustrated more closely in FIG. 2, activation of the motor 108 is achieved when the button 106 is pushed inwardly by the user. When the button 106 is pushed, the button 106 pushes a circuit contact 143 towards a battery contact 140 and a motor contact 142 such that an electrical circuit between the two is completed. The button 106 and/or the circuit contact 143 are normally biased outwardly (either by the use of a spring or resilient material [not shown]) such that when the button 106 is released the electrical circuit between the battery contact 140 and the motor contact 142 is broken causing the motor to automatically turn off. The device may have separate on/off buttons.

Figure 4:
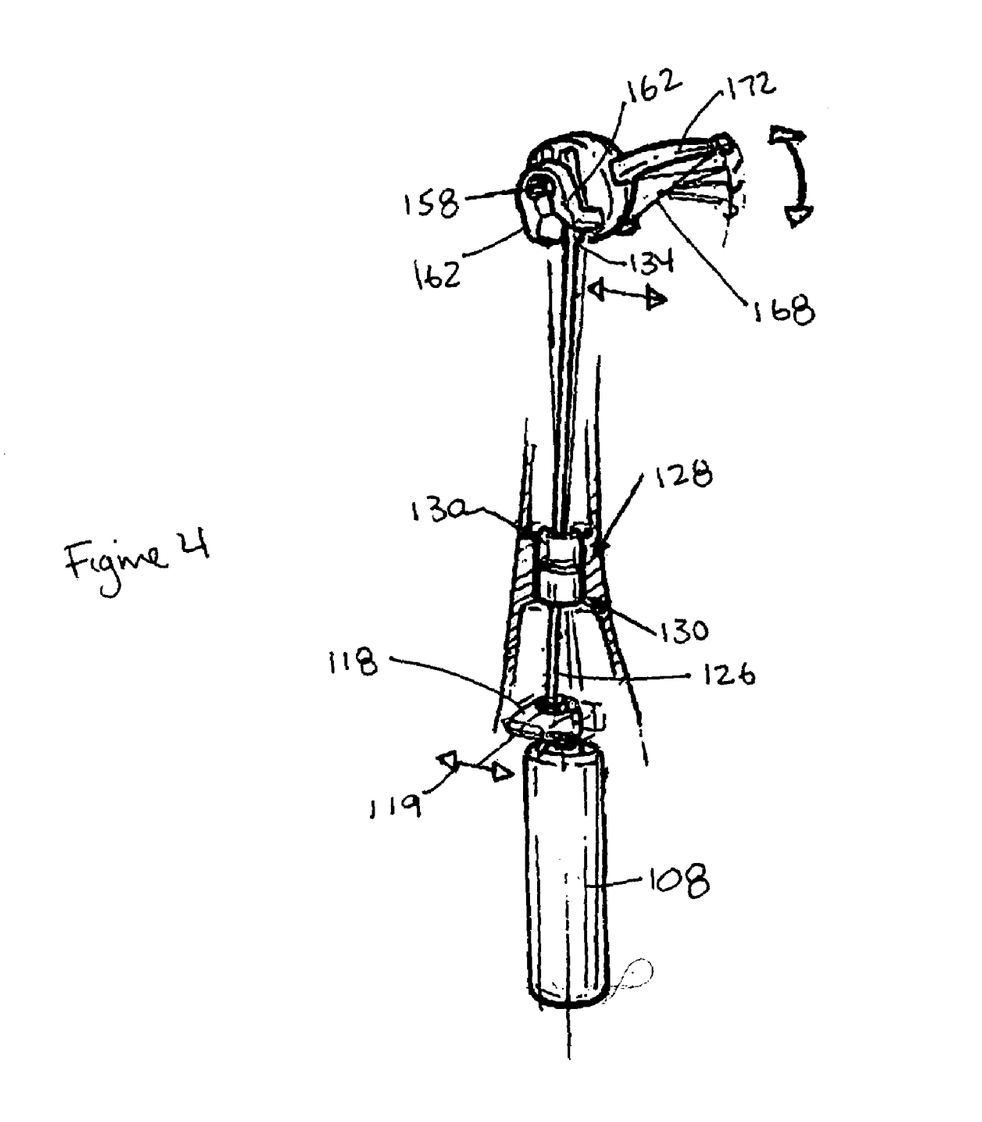
FIG. 4 is a perspective view of the motion linkage and a flossing head in the device of FIG. 1.

Continuing to refer to FIGS. 1 and 4, the head support 136 may be designed to receive removable head assemblies, such that various oral cleaning instruments may be employed, such as, but not limited to, various brushing head assemblies (described in detail below) and/or various flossing head assemblies.

In one aspect of the present invention, the head support 136 receives a removable flossing head assembly 150. The flossing head assembly 150 includes a flossing head housing 152 with a locking flange 154 that slides into engagement with an aperture 138 on the head support 136. To disengage the flossing head assembly 150, the user presses the locking flange 154 while pulling the flossing head assembly 150 away from the head support 136.

The flossing head assembly 150 further includes a flossing head 156 that is rotatably secured about a pin 158 on the flossing head housing 152. A tension spring 160 may be placed between the flossing head 156 and the flossing head housing 152. Engaged or secured to the flossing head 156 are walls 162. The second end 134 of the rod 126 is placed between the walls 162 in order to assist in transposing the side-to-side motion of the second end 134 of the rod 126 into a counterclockwise and clockwise oscillating motion of the flossing head 156. As the second end 134 of the rod 126 moves side-to-side, the second end 134 alternately contacts and pushes the walls 162 outwardly from its center axis of rotation (the pin 158). The force against the walls 162 will cause the flossing head 156 to oscillate about the pin 158. The oscillating motion will also cause a flossing tool 164 attached to the flossing head 156 to oscillate counterclockwise and clockwise. The flossing head 156 is retained in the flossing head housing by one or more retainer pins 166.

The flossing tool 164 has a section of flossing material 168 stretched over a cavity 170 that is created between two opposable arms 172, which extend from a support region 174. The support region 174 frictionally fits into a channel 176 on the flossing head 156, thereby permitting a used flossing tool 164 to be replaceable.

The flossing head 156 is also secured perpendicularly to the device 100 such that the flossing tool 164 extends perpendicularly away from the device 100. However, the flossing head or flossing tool 164 may be secured at various angles offset from the axis of the device 100.

Figure 5A:
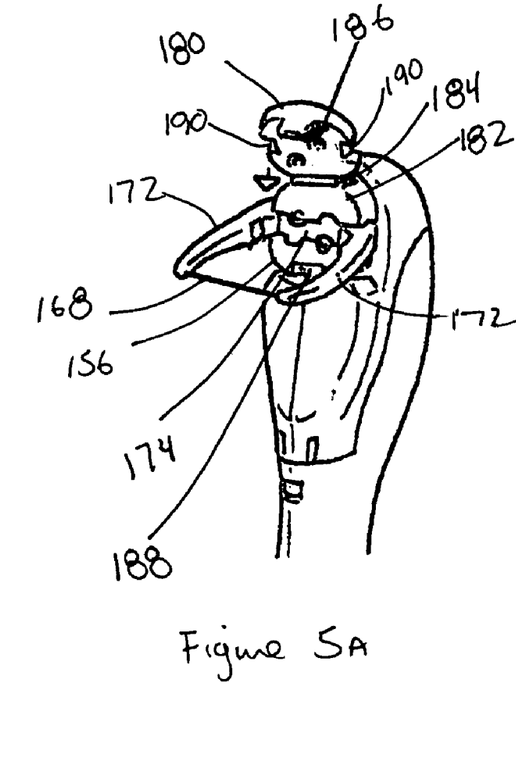
FIG. 5a is a perspective view of another flossing head with an opened retaining cap.
Figure 5B:
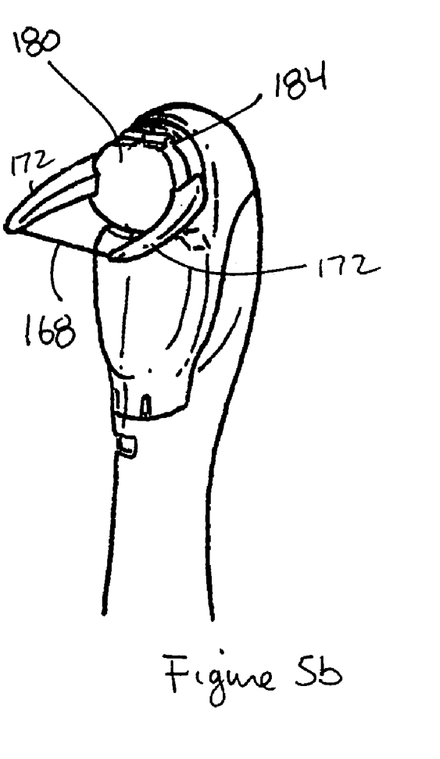
FIG. 5b is a perspective view of the flossing head of FIG. 5a with the retaining cap closed.

In another aspect of the present invention, the flossing head 156 may include a locking cap 180, illustrated in FIGS. 5a and 5b. The locking cap 180 is hinged 184 on one side to the face 182 of the flossing head 156. The locking cap 182 would also include a tab 186 that frictionally fits into a corresponding detent 188 on the face 182 of the flossing head 156. The locking cap 180 prevents the flossing tool 164 from separating from the flossing head 156. In addition, the locking cap 180 also includes side grooves 190 that receive the opposing arms 172 of flossing tool 164 and presses the arms 172 outwardly from each other to maintain a taut flossing material 168.

Figures 6A, 6C:
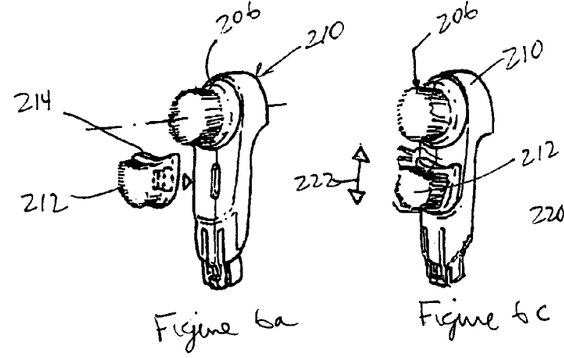
FIGS. 6a and 6b are front and back perspective views of another brush head assembly interchangeable with the head assemblies of the device of FIG. 1 and having oscillating bristles and non-oscillating but movable bristles.
FIG. 6c is a perspective view of the brush head assembly from FIG. 6a illustrating the movement of the non-oscillating but movable bristles.
Figure 6B:
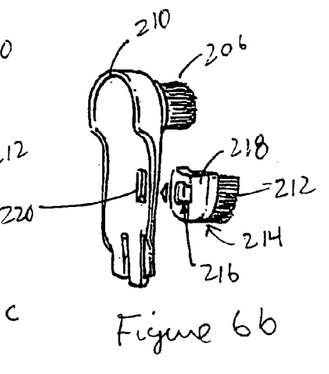

In another aspect of the present invention illustrated in FIG. 6a through 6c, a brush head assembly 210 may employ oscillating bristles 206 movably controlled by the motor described herein above. The brush head assembly 210 also includes nonoscillating but movable bristles 212. The nonoscillating but movable bristles 212 are secured to a secondary brush head 214 that includes a protrusion 216 on the backside 218 thereof. The protrusion 216 fits into a slot 220 positioned on the brush head assembly 210 that permits the secondary brush head 214 to freely slide within the slot 220. During use, the secondary brush head 214 will move along the slot 220 towards and away from the oscillating bristles 206 (illustrated by arrows 222 in FIG. 6c) when the user presses the secondary brush head 214 onto its teeth and moves the device 100.

Figure 7:
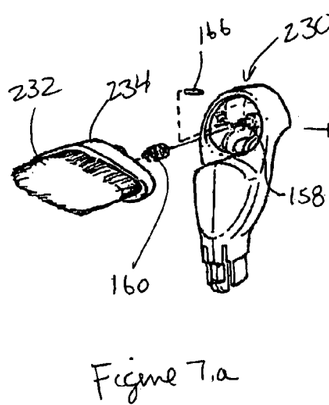
FIGS. 7a and 7b are front and back perspective views of another brush head assembly with an oval oscillating brush head with the oval brush head being attached with its longitudinal axis being aligned perpendicular with axis of the brush head assembly.
FIG. 7c is a front view of the oval brush head assembly of FIG. 7a, illustrating the movement of the brush head.
Figure 7B:
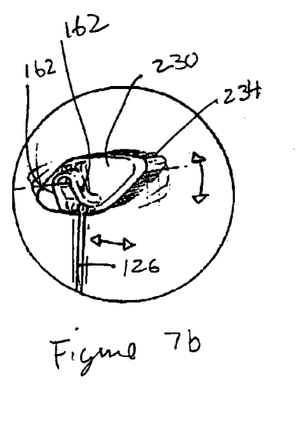
Figure 7C:
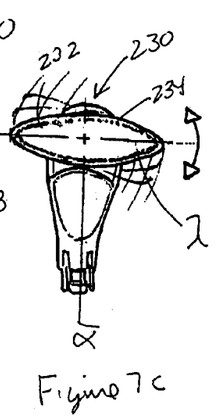

In yet another aspect of the invention (FIGS. 7a through 7c), a brush head assembly 230 may include oscillating bristles 232 attached to an oval brush head 234. The oval brush head 234 is secured to the brush head assembly 230 similarly to that which has been previously described. In addition the oval brush head 234 is orientated such that the longitudinal axis λ (its long axis) is aligned to be perpendicular to the axis (referenced as α in FIG. 7c) of the brush head assembly 230. As such, the orientation and oscillation of the oval brush head 234 would allow for a good cleaning of the user's tongue.

Figure 8A:
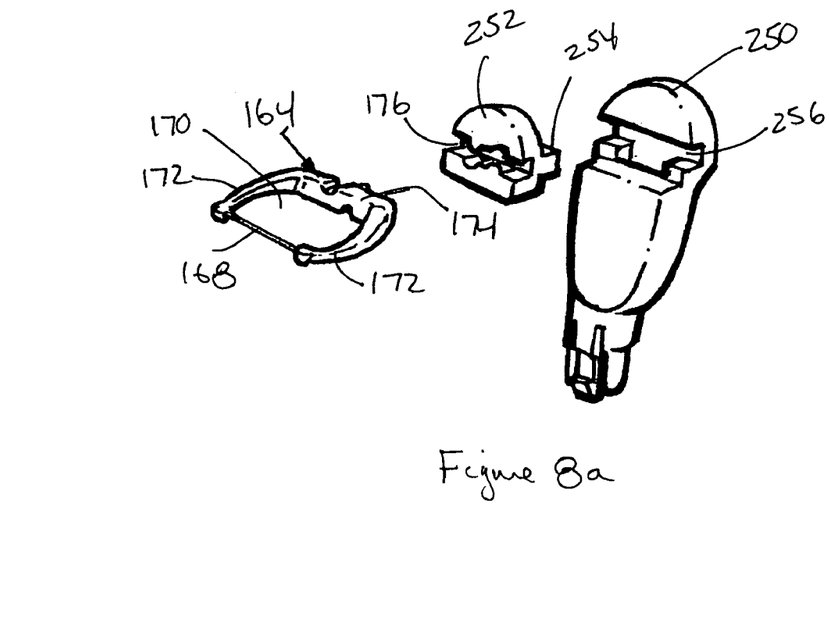
FIG. 8a is a front perspective view of another flossing head assembly with a side-to-side movement of the flossing tool.
Figure 8B:
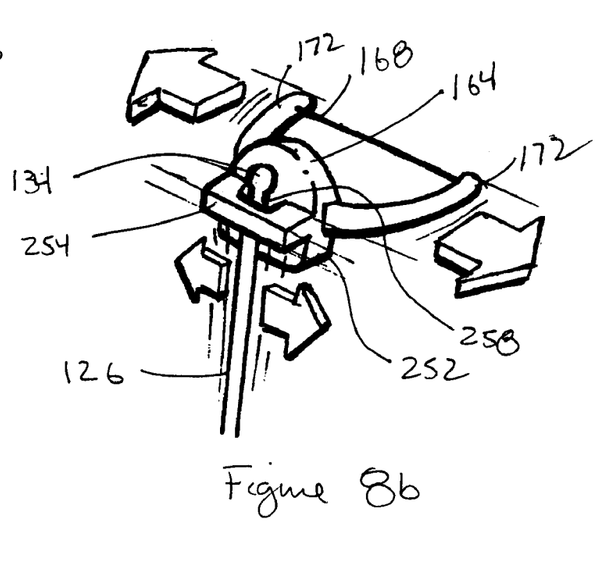

In yet another aspect of the invention (FIGS. 8a and 8b) a flossing head assembly 250 may include side-to-side motion, rather than the oscillating motion. The flossing head assembly 250 includes a moveable section 252, which has a bracket 254 on the backside thereof. The bracket 254 slides within a groove 256 defined by the flossing head assembly 250. A disposable flossing tool 164 is in removable engagement with the moveable section 252, as previously described. As shown in FIG. 8b, the second end 134 of the rod 126 is inserted into an opening 258 defined by the bracket 254 on the backside 254 of the moveable section 252. When the second end 134 is moving in the side-to-side motion, the moveable section 252 will also move in a back and forth or side-to-side motion, causing the same movement in the flossing tool 164. Moreover, the moveable section 252 will also be secured within the groove 256 by virtue of the second end 134 being inserted into the bracket 254; as movement of the moveable section will be limited to the movement of the second end.

Figure 9:
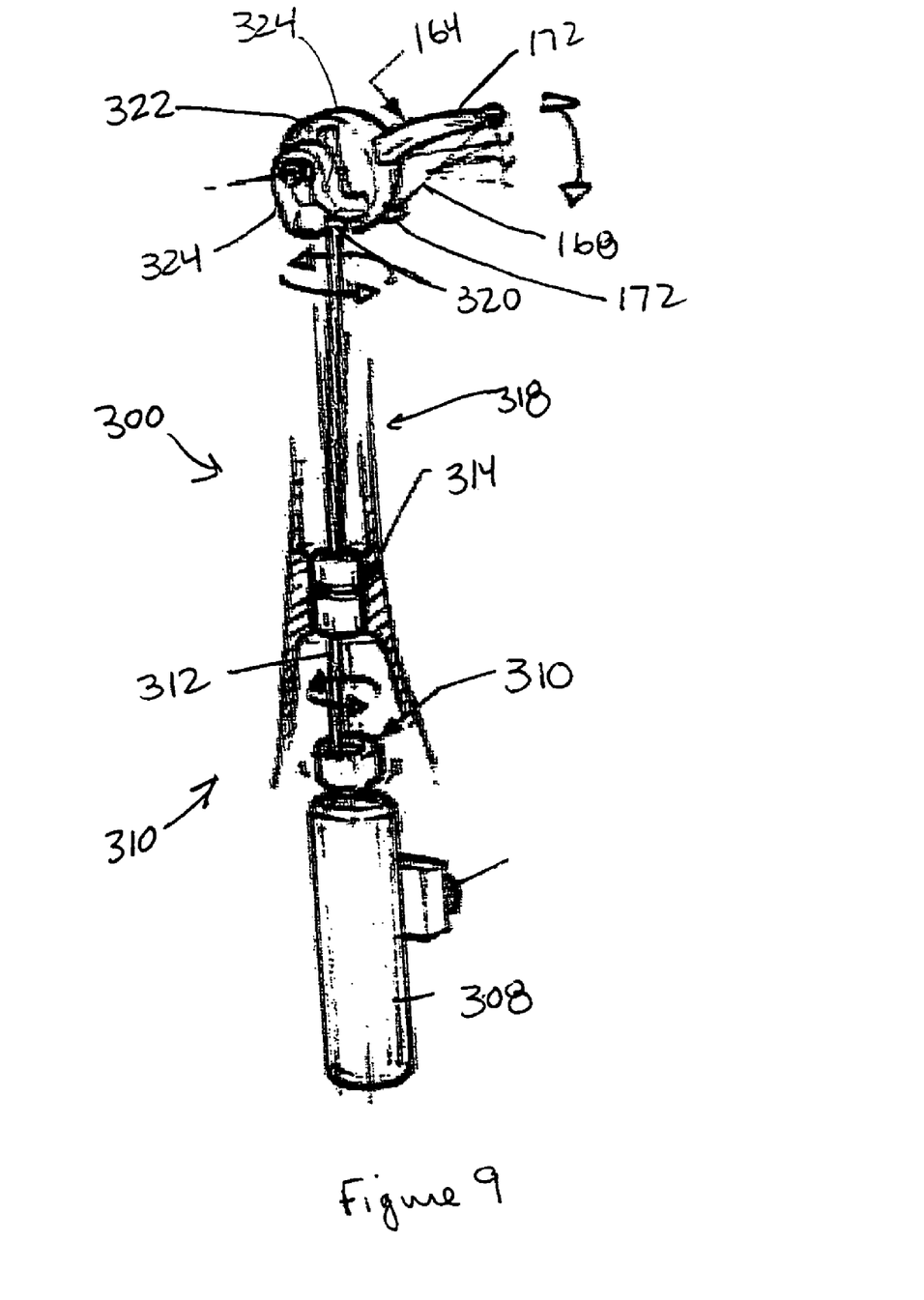
FIG. 9 is a perspective view of a motion linkage in accordance with a second embodiment of the present invention and illustrating a flossing head.

Referring now to FIG. 9, in a second embodiment, an electric oral cleaning device is illustrated and generally referenced to as 300. The device 300 is similar to the first embodiment 100 except that the motor 308 drives a differently configured linkage mechanism 309. In the second embodiment device 300, the motor 308 drives a cam 310 that has secured thereto at an offset position the first end of a rod 312. Secured along the length of the rod is a fulcrum 314. The rod 312 extends through a neck 318 of the device 300 and has a second end 320 that extends into the head support (as illustrated in FIG. 1). This configuration tends to transpose the rotational motion of the motor 308 to a circular motion in the second end 320 of the rod 312.

Figure 10A:
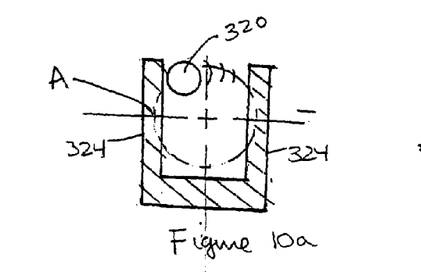
FIGS. 10a–10d are top views illustrating the movement of the second end of the rod of FIG. 9 and its contact with the walls that may be secured to a head.
Figure 10B:
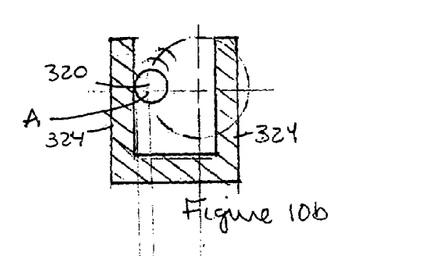
Figure 10C:
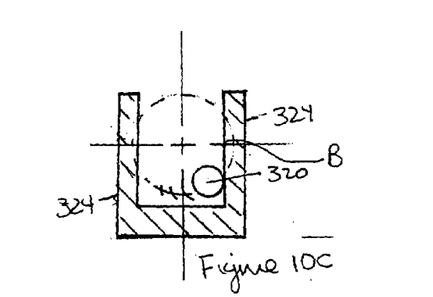
Figure 10D:
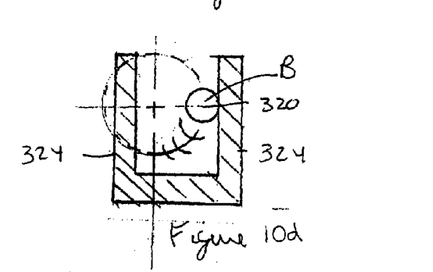
Figure 11A:
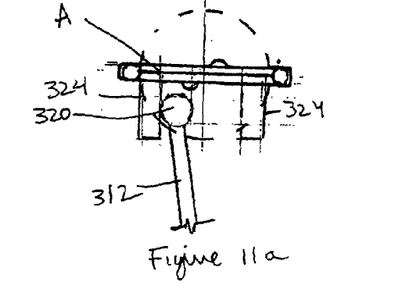
FIGS. 11a–11d are side views corresponding to 10a–10d illustrating movement of the second end of the push rod and its effect on a flossing tool.
Figure 11B:
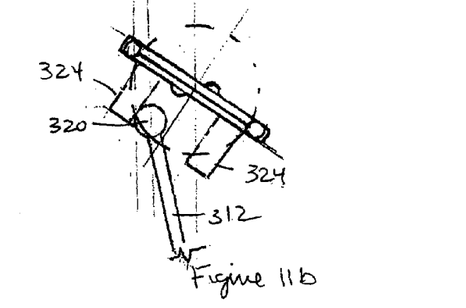
Figure 11C:
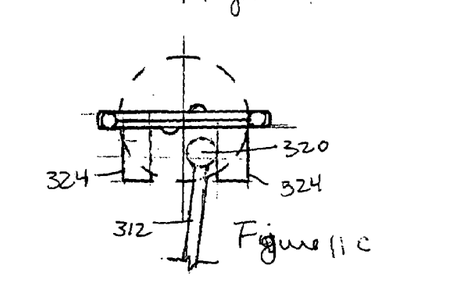
Figure 11D:
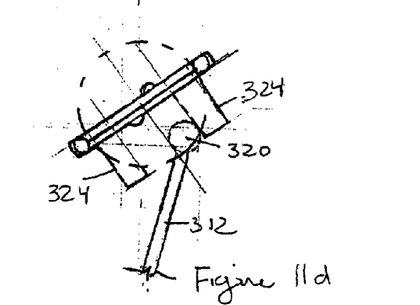

Referring now to FIGS. 10a through 10d and corresponding FIGS. 11a through 11d, as the second end 320 of the rod 312 moves in a circular direction and as the second end 320 approaches point A on its circular motion (FIGS. 10a and 11a) it contacts walls 324 secured to the flossing head 156 (or other head attached thereto). Once the second end 320 contacts one of the walls 324, the flossing head 156 will move about the pin 158 in the direction the second end 320 is traveling (FIGS. 10b and 11b). This causes one of the flossing arms 172 to be in a higher position then the other arm. Similarly, as the second end 320 continues to move to the opposite point B on its circular motion (FIGS. 10c and 11c), the second end 320 contacts the walls 324 causing the flossing head 156 to move in an opposite direction, (FIGS. 10d and 11d). The back and forth oscillating motion of the flossing head 156 acts to move the flossing tool 164 (and thus the flossing material 168) in a fluttering like motion.

From the foregoing and as mentioned above, it will be observed that numerous variations and modifications may be effected without departing from the spirit and scope of the novel concept of the invention. It is to be understood that no limitation with respect to the specific embodiments illustrated herein is intended or should be inferred.

I claim:

1. An electric flosser comprising:
a body having a handle portion and a head portion, the head portion including a movable section rotatably connected to a pin extending from said head portion;
an electrically operated motor in said handle portion;
a means interconnecting said motor and said movable section to rotationally oscillate said movable section in a clockwise and counterclockwise direction about said pin in said head portion;
a channel defined on said movable section; and
a flossing tool having a section in removable engagement with said channel,
whereby when said motor is operated the flossing tool is oscillated in a clockwise and counterclockwise direction.

2. The electric flosser of claim 1, wherein the head portion includes a locking flange and the body includes a notch that receives said locking flange to place the head portion in removable engagement with the body.

3. The electric flosser of claim 1 further comprising a cap hinged to said movable section, said cap and said movable section include a means to secure the cap in a closed position over said channel when the section of said flossing tool is in functional engagement therewith, wherein said closed position prevents the flossing tool from separating from said movable section.

4. The electric flosser of claim 3, wherein the cap includes side elements that engage and push a pair of opposable arms defined by the flossing tool outwardly from each other when said cap is in said closed position.

5. The electric flosser of claim 1, wherein the motor rotates a cam that moves a carrier attached thereto in a side-to-side motion, the carrier includes an aperture to receive a rod that extends upwards through the head portion to engage and move the movable section in a counterclockwise and clockwise oscillation.

6. An electric oral cleaning device comprising:
a body having a handle portion, a head assembly and a neck portion intermediate the handle portion and head assembly, the head assembly having a movable section rotatably connected thereto;
an electrically operated motor in said handle portion;
a means interconnecting said motor and said movable section to oscillate said movable section in a clockwise and counterclockwise direction;
the head assembly having a locking flange and the body having a notch that receives said locking flange to place the head assembly in removable engagement with the body, such that the head assembly is interchangeable with a second head assembly having a different configuration;
the head assembly having a channel defined on said movable section and having a flossing tool that includes a region in removable engagement with said channel, whereby when the motor is operated the flossing tool is oscillated; and
a cap hinged to said movable section, said cap and said movable section include a means to secure the can in a closed position, over said channel when the section of said flossing tool is in functional engagement therewith, wherein said closed position prevents the flossing tool from separating from said movable section.

7. The electric oral cleaning device or claim 6, wherein the cap includes side elements that engage and push a pair of opposable arms defined by the flossing tool outwardly from each other when said cap is in said closed position.

8. The electric oral cleaning device of claim 6, wherein the second head assembly includes a first movable section engaged with said means interconnecting said motor thereto to oscillate said first movable section counterclockwise and clockwise, the first movable section includes bristles secured thereto, the head assembly having a second movable section that is freely attached to the head assembly such that the second movable section moves independently of the first movable section, the second movable section includes bristles secured thereto.

9. The electric oral cleaning device of claim 6, wherein the interconnecting means includes a cam rotatably connected to said motor and a carrier engaged to said cam and slidably attached to the body such that the rotational motion of the cam is transposed to a side-to-side motion, the carrier includes an aperture to receive a rod that extends to the head assembly to engage and move the movable section in a counterclockwise and clockwise oscillation.

* * * * *